United States Patent [19]

Karrer

[11] 4,322,531
[45] Mar. 30, 1982

[54] DIAZAPHOSPHOLANES AND DIAZAPHOSPHORINANES

[75] Inventor: Friedrich Karrer, Zofingen, Switzerland

[73] Assignee: Ciba-Geigy Corporation, Ardsley, N.Y.

[21] Appl. No.: 188,400

[22] Filed: Sep. 18, 1980

[30] Foreign Application Priority Data

Sep. 27, 1979 [CH] Switzerland ............... 8720/79

[51] Int. Cl.³ .................................. C07D 211/58
[52] U.S. Cl. ......................................... 546/22; 546/24
[58] Field of Search ........................... 546/21, 22, 24

[56] References Cited

U.S. PATENT DOCUMENTS 3,684,765  8/1972  Matsui et al. .............. 260/45.8 N
3,904,581  9/1975  Murayama et al. ......... 260/45.8 N
3,970,636  7/1976  Hardy et al. ............... 260/45.8 NE

FOREIGN PATENT DOCUMENTS 2335520  7/1977  France .

*Primary Examiner*—John M. Ford
*Attorney, Agent, or Firm*—Harry Falber

[57] ABSTRACT

The invention relates to diazaphospholanes and diazaphosphorinanes of the formula I

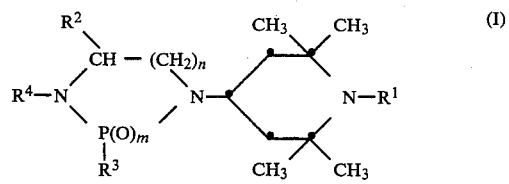

in which m is 0 or 1, n is 1 or 2 and $R^1$ to $R^4$ are as defined in claim 1. These compounds are effective light stabilizers for organic materials, especially for polymers. In addition, they can also possess an antioxidant and/or a flame retardant action. They can be obtained from the corresponding diamines by a cyclization reaction with the phosphorus dichlorides $R^3P(O)_mCl_2$.

4 Claims, No Drawings

DIAZAPHOSPHOLANES AND DIAZAPHOSPHORINANES

The present invention relates to novel diazaphospholane and diazaphosphorinane derivatives, the ring nitrogens of which carry at least one polyalkylpiperidine radical, and to the use of these compounds as light stabilisers for organic polymers, and to the material stabilised therewith.

The compounds of this invention have the formula I

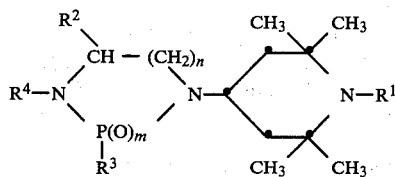

in which m is 0 or 1, n is 1 or 2, $R^1$ is hydrogen, oxygen, $C_1$–$C_{12}$alkyl, $C_3$–$C_5$alkenyl, propargyl, $C_7$–$C_{11}$phenylalkyl, $C_8$–$C_{15}$alkylphenylalkyl, $C_2$–$C_4$hydroxyalkyl, $C_4$–$C_{10}$acyloxyalkyl, cyanomethyl, $C_1$–$C_4$alkanoyl or $C_3$–$C_4$alkenoyl, $R^2$ is hydrogen or methyl, $R^3$ is $C_1$–$C_{12}$alkyl, $C_2$–$C_7$alkenyl, $C_6$–$C_{12}$aryl, $C_7$–$C_{11}$phenylalkyl, styryl, phenyl substituted by $C_1$–$C_4$alkyl, $C_5$–$C_6$cycloalkyl, 2-cyclohexylvinyl, $C_1$–$C_{12}$alkoxy, $C_2$–$C_6$alkenyloxy, phenoxy, phenoxy substituted by $C_1$–$C_4$alkyl, $C_7$–$C_{11}$phenylalkoxy, $C_5$–$C_6$cycloalkoxy or —$NR^5R^6$ and $R^4$ is hydrogen, $C_1$–$C_4$alkyl, $C_5$–$C_6$cycloalkyl, phenyl, or a group of the formula II,

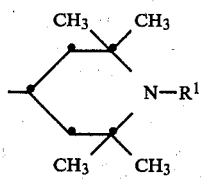

and each of $R^5$ and $R^6$ independently is hydrogen, $C_1$–$C_{12}$alkyl, $C_3$–$C_5$alkenyl, cyclohexyl or phenyl, or $R^5$ and $R^6$ together are $C_4$–$C_5$alkylene or 3-oxapentyl-1,5-ene.

When n is 1, these compounds are derivatives of 1,3,2-diazaphospholane; and when n is 2, they are derivatives of 1,3,2-diazaphosphorinane.

When m is 0, the compounds contain trivalent phosphorus; and when m is 1, they are compounds of pentavalent phosphorus.

$R^1$, $R^3$, $R^5$ and $R^6$ as alkyl can be branched or unbranched alkyl groups, for example methyl, ethyl, isopropyl, tert-butyl, hexyl, 2-ethylhexyl, octyl, isononyl, decyl or dodecyl.

$R^1$, $R^5$ and $R^6$ as alkenyl can be e.g. allyl, methallyl, crotyl or 2-methyl-2-butenyl. $R^3$ as alkenyl can also be e.g. vinyl, 1-propenyl, 1-isobutenyl, 1-hexenyl, or 4,4-dimethylpent-1-enyl.

$R^1$ as hydroxyalkyl can be 2-hydroxyethyl, 2-hydroxypropyl or 2-hydroxybutyl. $R^1$ as acyloxyalkyl can be, for example, 2-acetoxyethyl, 2-butyroyloxypropyl or 2-benzoyloxyethyl. $R^1$ as acyl can be e.g. formyl, acetyl, propionyl, acryloyl or butyroyl.

$R^1$ and $R^3$ as phenylalkyl can be e.g. benzyl, 1-phenylethyl, 2-phenylethyl, 1-phenylisopropyl, 3-phenylpropyl or 4-phenylbutyl.

$R^1$ as alkylphenylalkyl can be e.g. 4-methylbenzyl, 3-isopropylbenzyl, 4-t-butylbenzyl, 2-(4'-butylphenyl)-ethyl or 3,5-dimethylbenzyl.

$R^3$ as alkoxy can be branched or unbranched alkoxy, e.g. methoxy, ethoxy, isopropoxy, sec-butoxy, hexyloxy, octyloxy or dodecyloxy. $R^3$ as alkenyloxy can be e.g. vinyloxy, allyloxy or 1-hexenyloxy.

$R^3$ as phenylalkoxy can be e.g. benzyloxy or 3-phenylpropoxy.

It is known to use polyalkylpiperidine derivatives as light stabilisers, especially for organic polymers. German Offenlegungsschriften Nos. 2 040 975 and 2 349 962 describe 4-amino derivatives of polyalkylpiperidines and their N-alkyl and N-acyl derivatives as light stabilisers, but do not describe any N-phosphonyl derivatives. Many of these known 4-aminopiperidine derivatives tend to discolour on warming and others are relatively ineffective. In contrast, the compounds of the formula I do not tend to discolour and have a very pronounced light stabilising action. In addition, the compounds in which m=0 also have a certain, or a considerable, antioxidant action.

Preferred compounds are those of the formula I in which m is 1, n is 1 or 2, $R^1$ is hydrogen, $C_1$–$C_4$alkyl, $C_3$–$C_5$alkenyl or benzyl, $R^2$ is hydrogen, methyl or allyl, $R^3$ is $C_1$–$C_6$alkyl, $C_2$–$C_7$alkenyl, cyclohexyl, phenyl, $C_1$–$C_6$alkoxy, $C_3$–$C_4$alkenyloxy, cyclohexyloxy, phenoxy or phenoxy substituted by $C_1$–$C_4$alkyl, and $R^4$ is hydrogen, $C_1$–$C_4$alkyl, cyclohexyl, phenyl or a group of the formula II.

Particularly preferred compounds are those of the formula I in which m is 1, n is 1 or 2, $R^1$ is hydrogen, methyl, allyl or benzyl, $R^2$ is hydrogen or methyl, $R^3$ is $C_1$–$C_4$alkyl, cyclohexyl, phenyl, $C_1$–$C_4$alkoxy, cyclohexyloxy or phenoxy and $R^4$ is hydrogen, $C_1$–$C_4$alkyl, cyclohexyl, phenyl or a group of the formula II. Compounds in which $R^4$ is a group of the formula II are most preferred.

Examples of compounds of the formula I are 1,3-bis-(2,2,6,6-tetramethylpiperid-4-yl)-2-methyl-2-oxo-1,3,2-diazaphospholane, 1,3-bis-(2,2,6,6-tetramethylpiperid-4-yl)-2-benzyl-2-oxo-1,3,2-diazaphospholane, 1,3-bis-(2,2,6,6-tetramethylpiperid-4-yl)-2-cyclohexyl-2-oxo-1,3,2-diazaphospholane, 1,3-bis-(2,2,6,6-tetramethylpiperid-4-yl)-2-phenyl-2-oxo-1,3,2-diazaphospholane, 1,3-bis-(1-methyl-2,2,6,6-tetramethylpiperid-4-yl)-2-butyl-1,3,2-diazaphosphorinane, 1,3-bis-(1-benzyl-2,2,6,6-tetramethylpiperid-4-yl)-2-styryl-2-oxo-4-methyl-1,3,2-diazaphospholane, 1,3-bis-(1-[2-acetoxyethyl]-2,2,6,6-tetramethylpiperid-4-yl)-2-vinyl-2-oxo-4-methyl-1,3,2-diazaphosphorinane, 1,3-bis-(1-acetyl-2,2,6,6-tetramethylpiperid-4-yl)-2-(2-butylvinyl)-2-oxo-1,3,2-diazaphosphorinane, 1,3-bis-(1-acryloyl-2,2,6,6-tetramethylpiperid-4-yl)-2-(2-cyclohexylvinyl)-2-oxo-1,3,2-diazaphospholane, 1,3-bis-(2,2,6,6-tetramethylpiperid-4-yl)-2-phenyl-1,3,2-diazaphospholane, 1,3-bis-(1,2,2,6,6-pentamethylpiperid-4-yl)-2-methoxy-2-oxo-1,3,2-diazaphospholane, 1,3-bis-(1,2,2,6,6-pentamethylpiperid-4-yl)-2-phenoxy-2-oxo-1,3,2-diazaphospholane, 1,3-bis-(2,2,6,6-tetramethylpiperid-4-yl)-2-cyclohexyloxy-2-oxo-1,3,2-diazaphosphorinane, 1,3-bis-(1-allyl-2,2,6,6-tetramethylpiperid-4-yl)-2-methyl-2-oxo-1,3,2-diazaphospholane, 1,3-bis-(1-benzyl-2,2,6,6-tetramethylpiperid-4-yl)-2-methyl-2-oxo-1,3,2-diazaphospholane, 1,3-bis-(1,2,2,6,6-pentamethylpiperid-4-yl)-2-diethylamino- 2-oxo-1,3,2-diazaphospholane, 1,3-bis-(2,2,6,6-tetramethylpiperid-4-yl)-2-morpholino-2-oxo-4-methyl-1,3,2-diazaphospholane, 1,3-bis(1-benzyl-2,2,6,6-tetramethylpiperid-4-yl)-2-phenyl-1,3,2-diazaphospholane and 1,3-bis-(1-allyl-2,2,6,6-tetramethylpiperid-4-yl)-2-ethoxy-1,3,2-diazaphospholane, 1-(2,2,6,6-tetramethylpiperidyl-4-)-2-phenyl-3-cyclohexyl-1,3,2-diazaphosphorinane, 1-(2,2,6,6-tetramethylpiperidyl-4)-2-benzyl-2-oxo-1,3,2-diazaphospholane, 1-(1,2,2,6,6-pentamethylpiperidyl-4)-2,3-dibutyl-2-oxo-1,3,2-diazaphosphorinane.

The compounds of the formula I can be understood as constituting cyclic diamides of phosphonic acids, phosphonous acids, phosphoric acid monoesters or phosphorous acid monoesters. Accordingly, they can be obtained by reacting the corresponding dichlorides $R^3—P(O)_mCl_2$ with the corresponding diamines of the formula III

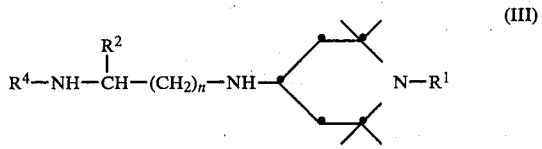
(III)

The reaction is preferably carried out in an inert solvent, for example benzene, toluene, xylene, tetrahydrofuran, chloroform, methylene chloride, 1,2-dichloroethane, dioxan or acetonitrile, with the addition of a base as a HCl acceptor. The base used can be an inorganic base, such as an alkali metal carbonate or alkali metal hydroxide, or a tertiary amine, for example triethylamine, diisopropylethylamine, tributylamine or pyridine.

Reaction of the diamines of formula III with one mole of $P(O)_mX_3$ in the presence of at least 2 equivalents of an anhydrous base yields the cyclic phosphorus halides of the formula IV

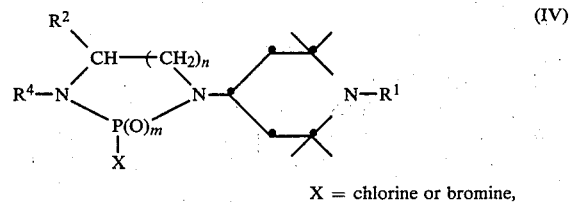
(IV)

X = chlorine or bromine,

These compounds do not need to be isolated, but can be reacted, in the same medium, with 1 mole of an alcohol or phenol (in the presence of 1 equivalent of a base) to give the compounds of the formula I, wherein $R_3$ is alkoxy, alkenyloxy, aryloxy, phenylalkoxy or cycloalkoxy.

In analogous manner, the reaction of compounds of the formula IV with 1 mole of an amine of the formula $R^5—NH—R^6$ gives compounds of the formula I, wherein $R^3$ is $—NR^5R^6$.

In one process variant, the radical $R^1$ can also be introduced subsequently. In this case, a diamine of the formula III, in which $R^1$ is hydrogen, is first reacted with a dichloride $R^3—P(O)Cl_2$ and the substituent $R^1$ is then introduced into the resulting compound of the formula I, in which $R^1$ is H. The introduction of the substituent $R^1$ can be effected by the procedures customary for N-substitutions, for example by reaction with alkyl halides, alkenyl halides or phenylalkyl halides. A methyl radical $R^1$ can also be introduced by reaction with formic acid/formaldehyde. The cyanomethyl radical can be introduced by reaction with formaldehyde and hydrocyanic acid or alkali metal cyanides. Hydroxyalkyl radicals can be introduced by reaction with alkylene oxides. Subsequent esterification of the hydroxyalkyl compounds results in the acyloxyalkyl compounds. The introduction of a N-acyl radical can be effected by reaction with carboxylic acid halides or carboxylic acid anhydrides. Compounds in which $R^1$ is an oxygen radical, and which are known as N-oxyls, are formed from the compounds containing hydrogen, by reaction with peroxy compounds, for example peroxycarboxylic acids, or by means of hydrogen peroxide in the presence of tungsten catalysts.

The diamines of the formula III are disclosed in German Offenlegungsschriften Nos. 2 611 208 and 2 349 962 and can be obtained by catalytic hydrogenation of the corresponding 4-oxopiperidines in the presence of primary diamines and the radical $R^1$ can be introduced before or after the hydrogenation.

The dichlorides $R—P(O)_mCl_2$ are generally known compounds, the preparation of which is described, for example, in Houben-Weyl, Methoden der Organischen Chemie (Methods of Organic Chemistry), G. Thieme-Verlag, Stuttgart 1964, volume XII/1, 302 and 387 and volume XII/2, 12 and 212.

The compounds of the formula I can be used as stabilisers for organic materials which are sensitive to the action of light. They possess a relatively high stability to heat. In addition to a pronounced light stabilising action, they also possess an antioxidant action, especially the compounds of the formula I containing trivalent phosphorus (m=0). The compounds of the formula I possess a certain flame retardant action, which can be intensified by combination with other flame retardants, for example halogen compounds.

Light-sensitive materials are, for example, fats and oils, photographic films and papers and cosmetic bases, but especially plastics and lacquers. Polymers on which such plastics and lacquers can be based are the following:

1. Polymers of mono- and diolefins, for example polyethylene (which can be crosslinked), polypropylene, polyisobutylene, polybut-1-ene, polymethylpent-1-ene, polyisoprene or polybutadiene, and polymers of cycloolefins, e.g. of cyclopentene or norbornene.

2. Mixtures of the polymers mentioned under (1), for example mixtures of polypropylene with polyethylene or with polyisobutylene.

3. Copolymers of mono- and diolefins with each other or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/alkylacrylate copolymers, ethylene/alkylmethacrylate copolymers, ethylene/vinyl acetate copolymers, or ethylene/acrylic acid copolymers and salts thereof (ionomers), and also terpolymers of ethylene with propylene and a diene, such as hexadiene, dicyclopentadiene or ethylidenenorbornene.

4. Polystyrene.

5. Copolymers of styrene or α-methylstyrene with dienes or acrylic derivatives, for example styrene/butadiene, styrene/acrylonitrile, styrene/alkylmethacrylate, styrene/acrylonitrile/methyl acrylate; mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene, or styrene-ethylene/propylene-styrene.

6. Graft copolymers of styrene, e.g. styrene with polybutadiene, styrene and acrylonitrile with polybutadiene, styrene and maleic anhydride with polybutadiene, styrene and alkyl acrylates or alkyl methacrylates with polybutadiene, styrene and acrylonitrile with ethylene-propylene-diene terpolymers, styrene and acrylonitrile with polyalkylacrylates or polyalkylmethacrylates, styrene and acrylonitrile with acrylate-butadiene copolymers, and mixtures thereof with the copolymers listed under (5), known e.g. as ABS, MBS, ASA or AES polymers.

7. Halogen-containing polymers, e.g. polychloroprene, chlorinated rubber, chlorinated or chlorosulfonated polyethylene, especially polymers of halogenated vinyl compounds, e.g. polyvinyl chloride, polyvinylidene chloride, polyvinyl fluoride, polyvinylidene fluoride, and their copolymers such as vinyl chloride/vinylidene chloride, vinyl chloride/vinyl acetate or vinylidene chloride/vinyl acetate.

8. Polymers which are derived from $\alpha,\beta$-unsaturated acids and their derivatives, such as polyacrylates and polymethacrylates, polyacrylamides and polyacrylonitriles.

9. Copolymers of the monomers listed in (8) with one another or with other unsaturated monomers, e.g. acrylonitrile/butadiene copolymers, acrylonitrile/alkyl acrylate copolymers, acrylonitrile/vinyl chloride copolymers, or acrylonitrile/alkyl methacrylate/butadiene terpolymers.

10. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinylbutyral, polyallyl phthalate, polyallylmelamine.

11. Homopolymers and copolymers of cyclic ethers such as polyethylene glycols, polyethylene oxide, polypropylene oxide or their copolymers with bis-glycidyl ethers.

12. Polyacetals such as polyoxymethylene, and also those polyoxymethylenes which contain a comonomer, e.g. ethylene oxide.

13. Polyphenylene oxides and sulfides.

14. Polyurethanes which are derived on the one hand from polyethers, polyesters and polybutadienes containing hydroxy end groups, and from aliphatic or aromatic polyisocyanates on the other, as well as their precursors.

15. Polyamides and copolyamides which are derived from diamines and dicarboxylic acids and/or from aminocarboxylic acids or the corresponding lactams, such as polyamide 4, polyamide 6, polyamide 66, polyamide 610, polyamide 11, polyamide 12, poly-2,4,4-trimethylhexamethyleneterephthalamide, poly-m-phenylene-isophthalamide, and their copolymers with polyethers, e.g. with polyethylene glycol, polypropylene glycol or polytetramethylene glycol.

16. Polyureas, polyimides and polyamide imides.

17. Polyesters which are derived from dicarboxylic acids and dialcohols and/or from hydroxycarboxylic acids or the corresponding lactones, such as polyethylene terephthalate, polybutylene terephthalate and poly-1,4-dimethylolcyclohexane terephthalate, and also block polyether esters which are derived from polyethers having hydroxyl end groups and dicarboxylic acids.

18. Polycarbonates.

19. Polysulfones and polyether sulfones.

20. Crosslinked polymers which are derived from aldehydes on the one hand and from phenols, ureas and melamines on the other hand, such as phenol-formaldehyde resins, urea-formaldehyde resins and melamine-formaldehyde resins.

21. Drying and non-drying alkyd resin.

22. Unsaturated polyester resins which are derived from copolyesters of saturated and unsaturated dicarboxylic acids with polyhydric alcohols and vinyl compounds as crosslinking agents, and also their halogen-containing modifications of low combustibility.

23. Crosslinkable acrylic resins which are derived from substituted acrylic esters, e.g. from epoxy acrylates, urethane acrylates or polyester acrylates.

24. Alkyd resins, polyester resins and acrylate resins which are crosslinked with melamine resins, urea resins, polyisocyanates or epoxy resins.

25. Crosslinked epoxy resins which are derived from polyepoxides, e.g. bis-glycidyl ethers, or from cycloaliphatic diepoxides.

26. Naturally occurring polymers, such as cellulose, rubber and gelatin, and also their polymer-homologously chemically modified derivatives, such as cellulose acetates, cellulose propionates and cellulose butyrates, and cellulose ethers such as methylcellulose.

Amongst these polymers, groups 1–6, 14, 15, 17, 23 and 24 are preferred, as the stabilisers of the invention have a particularly pronounced action in these substrates. In addition, polymers which are used as surface coating resins are of particular importance.

The stabilisers of the formula I are incorporated in the substrates in a concentration of 0.01 to 5% by weight and preferably 0.1 to 1% by weight, based on the material to be stabilised.

Incorporation can be effected, for example, by blending in at least one of the light stabilisers of the invention and, if desired, further additives, by the methods conventionally employed in the art, before or during shaping, or by applying the dissolved or dispersed compounds to the polymer, with subsequent evaporation of the solvent if necessary.

The plastics material stabilised in this way can also contain other stabilisers or other additives customarily employed in plastics technology, for example those listed on pages 25–32 of German Offenlegungsschrift No. 2 349 962.

Synergistic effects can result when known stabilisers are also used. This frequently occurs especially when other light stabilisers or organic phosphites are also used.

The additional use of antioxidants when stabilising polyolefins is of particular importance.

The invention therefore also relates to the plastics stabilised by the addition of 0.01 to 5% by weight of a compound of the formula I, which plastics can also contain other known and customary additives if desired. The plastics stabilised in this way can be used in a wide variety of forms, for example as films, fibres, tapes or profiles or as binders for lacquers, adhesives or putties.

Use in thin layers, as in the form of fibres, films and lacquers, is of particular importance.

The production and use of the compounds of the present invention are described in more detail in the following Examples, in which parts and percentages are by weight.

EXAMPLE 1

With stirring and while introducing $N_2$ gas, a solution of 16.5 g (0.125 mole) of methylphosphonyl dichloride in 30 ml of methylene chloride is added dropwise in the course of 2 hours at 0° C. to a solution of 40.6 g (0.12 mole) of N,N'-bis-(2,2,6,6-tetramethylpiperidin-4-yl)-diaminoethane and 40 ml of triethylamine in 140 ml of methylene chloride. The mixture is then slowly warmed to room temperature and stirring is continued overnight at room temperature.

For working up, precipitated triethylamine hydrochloride is collected by filtration and the solvent is completely distilled off in vacuo. The residue is dissolved in 500 ml of acetonitrile, 50 g of finely powdered potassium carbonate are added, and this mixture is stirred for 2 hours at room temperature and then filtered. The solvent is distilled off from the filtrate and the residue is recrystallised from cyclohexane/toluene (about 10:1), yielding pure 1,3-bis-(2,2,6,6-tetramethylpiperid-4-yl)-2-methyl-2-oxo-1,3,2-diazaphospholane (compound 1) with a melting point of 198°–199° C.

$C_{21}H_{43}N_4PO$ (398.54): calculated: C 63.28; H 10.07; N 14.06; P 7.77%; found: C 63.3; H 10.0; N 14.3; P 7.7%.

The following compounds were prepared analogously:

1,3-bis(1,2,2,6,6-pentamethylpiperidyl-4)-2-methyl-2-oxo-1,3,2-diazaphospholane (compound 2) with a melting point of 182°–184° C.

1,3-bis(2,2,6,6-tetramethylpiperidyl-4)-2-cyclohexyl-2-oxo-1,3,2-diazaphospholane (compound 3) with a melting point of 151°–153° C.

1,3-bis(2,2,6,6-tetramethylpiperidyl-4)-2-phenyl-2-oxo-1,3,2-diazaphospholane (compound 4) with a melting point of 187°–189° C.

1,3-bis(2,2,6,6-tetramethylpiperidyl-4)-2-butoxy-2-oxo-1,3,2-diazaphospholane (compound 5) with a melting point of 56°–58° C.

1,3-bis(2,2,6,6-tetramethylpiperidyl-4)-2-phenoxy-2-oxo-1,3,2-diazaphospholane (compound 6) with a melting point of 110°–112° C.

1,3-bis-(2,2,6,6-tetramethylpiperidyl-4)-2-(4,4-dimethylpent-1-enyl-1)-2-oxo-1,3,2-diazaphospholane (compound 7) with a melting point of 98°–100° C.

1,3-bis(2,2,6,6-tetramethylpiperidyl-4)-2-phenyl-1,3,2-diazaphospholane (compound 8) with a melting point of 165° C.

EXAMPLE 2

In accordance with the procedure of Example 1, N,N'-bis(2,2,6,6-tetramethylpiperidinyl-4-)-1,2-diaminopropane is reacted with $CH_3P(O)Cl_2$ to give 1,3-bis(2,2,6,6-tetramethylpiperidyl-4-)-2-methyl-2-oxo-4-methyl-1,3,2-diazaphospholane (compound 9) with a melting point of 158°–162° C.

EXAMPLE 3

In accordance with the procedure of Example 1, N,N'-bis(2,2,6,6-tetramethylpiperidyl-4-)-1,3-diaminopropane is reacted with $C_3H_7P(O)Cl_2$ to give 1,3-bis(2,2,6,6-tetramethylpiperidyl-4-)-2-propyl-2-oxo-1,3,2-diazaphosphorinane (compound 10) with a melting point of 163°–169° C.

EXAMPLE 4

In accordance with the procedure of Example 1, N,N'-bis(1,2,2,6,6-pentamethylpiperidyl-4-)-1,3-diaminopropane is reacted with $C_6H_5P(O)Cl_2$ to give 1,3-bis(1,2,2,6,6-pentamethylpiperidyl-4-)-2-phenyl-2-oxo-1,3,2-diazaphosphorinane (compound 11) with a melting point of 155°–156° C.

EXAMPLE 5

In accordance with the procedure of Example 1, N-cyclohexyl-N'-(2,2,6,6-tetramethylpiperidyl-4-)-1,3-diaminopropane is reacted with $C_6H_5P(O)Cl_2$ to give 1-(2,2,6,6-tetramethylpiperidyl-4-)-2-phenyl-2-oxo-3-cyclohexyl-1,3,2-diazaphosphorinane (compound 12) with a melting point of 126°–127° C.

EXAMPLE 6

A mixture of 19.9 g (0.05 mole) of 1,3-bis-(2,2,6,6-tetramethylpiperid-4-yl)-2-methyl-2-oxo-1,3,2-diazaphospholane (compound 1), 16.6 g of potassium carbonate, 0.3 g of finely powdered potassium iodide, 24.2 g of allyl bromide and 80 ml of ethyl methyl ketone is stirred for 18 hours at reflux temperature. The mixture is then filtered, the filtrate is freed from the solvent in vacuo and the residual crystalline crude product is recrystallised from acetonitrile, yielding pure 1,3-bis(1-allyl-2,2,6,6-tetramethylpiperid-4-yl)-2-methyl-2-oxo-1,3,2-diazaphospholane (compound 13) with a melting point of 168°–169° C.

$C_{27}H_{51}N_4PO$ (478.7) calculated: C 67.74; H 10.74; N 11.70%; found: C 67.7; H 10.6; N 11.7%.

The following compounds were obtained in analogous manner:

(a) 1,3-bis-(1-allyl-2,2,6,6-tetramethylpiperidyl-4)-2-phenyl-2-oxo-1,3,2-diazaphospholane (compound 14) with a melting point of 141°–142° C., from compound 4 and allyl bromide;

(b) 1,3-bis-(1-benzyl-2,2,6,6-tetramethylpiperidyl-4)-2-methyl-2-oxo-1,3,2-diazaphospholane (compound 15) with a melting point of 154°–156° C., from compound 1 and benzyl bromide.

EXAMPLE 7

Stabilisation of propylene against light 100 parts of polypropylene powder (Moplen, fibre grade, manufactured by Montedison), 0.2 part of β-(3,5-di-tert-butyl-4-hydroxyphenyl)-propionic acid octadecyl ester and 0.25 part of a stabiliser of Table 1 are homogenised in a Brabender plastograph for 10 minutes at 200° C. The resultant plastic mass is removed from the kneader as quickly as possible and pressed to a 2–3 mm sheet in a toggle press. A portion of the sheet is cut out and pressed between two ultra-gloss rigid aluminium sheets with a hand-operated hydraulic laboratory press for 6 minutes at 260° C. to a 0.1 mm sheet, which is immediately chilled in cold water. Segments are then punched out of this sheet and exposed in the xenotest 1200. These samples are taken out of the exposure apparatus at regular intervals and examined for their carbonyl content in a IR spectrophotometer. The increase in the carbonyl extinction at 5.85μ during exposure is a reference value for the degradation of the polymer by photooxidation [see L. Balaban et al., J. Polymer Sci., Part C; 22, 1059–1071 (1969] and, as experience shows, is associated with a decrease in the mechanical properties of the polymer. The time taken till a carbonyl extinction of about 0.3 is reached, at which value the comparison sheet is brittle, serves as an indication of the protective action.

The ratio of this exposure time to the exposure time in a blank test without stabiliser is the protective factor PF:

$$PF = \frac{\text{exposure time using sample}}{\text{exposure time in blank test}}$$

The protective factors of the investigated stabilisers are reported in the following table:

| Stabilisor | Protective factor PF |
|---|---|
| none | 1 |
| compound 1 | 8.1 |
| compound 2 | 9.5 |
| compound 3 | 7.3 |
| compound 13 | 7.5 |

What is claimed is:

1. A compound of the formula I

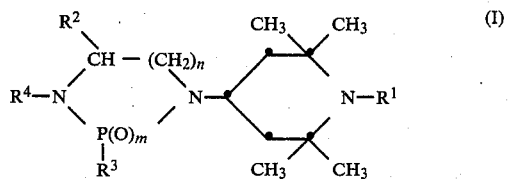

in which m is 0 or 1, n is 1 or 2, $R^1$ is hydrogen, oxygen, $C_1$-$C_{12}$alkyl, $C_3$-$C_5$alkenyl, propargyl, $C_7$-$C_{11}$phenylalkyl, $C_8$-$C_{15}$alkylphenylalkyl, $C_2$-$C_4$hydroxyalkyl, $C_4$-$C_{10}$alkanoyloxyalkyl, cyanomethyl, $C_1$-$C_4$alkanoyl or $C_3$-$C_4$alkenoyl, $R^2$ is hydrogen or methyl, $R^3$ is $C_1$-$C_{12}$alkyl, $C_2$-$C_7$alkenyl, $C_6$-$C_{12}$aryl, $C_7$-$C_{11}$phenylalkyl, phenyl substituted by $C_1$-$C_4$alkyl, $C_5$-$C_6$cycloalkyl, $C_1$-$C_{12}$alkoxy, $C_2$-$C_6$alkenyloxy, phenoxy, phenoxy substituted by $C_1$-$C_4$alkyl, $C_7$-$C_{11}$phenylalkoxy $C_5$-$C_6$cycloalkoxy or —$NR^5R^6$, and $R^4$ is hydrogen, $C_1$-$C_4$alkyl, $C_5$-$C_6$cycloalkyl phenyl, or a group of the formula II

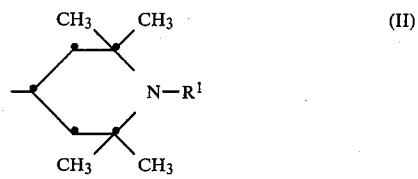

and each of $R^5$ and $R^6$ independently is hydrogen, $C_1$-$C_{12}$alkyl, $C_3$-$C_5$alkenyl, cyclohexyl or phenyl, or $R^5$ and $R^6$ together are $C_4$-$C_5$alkylene.

2. A compound according to claim 1 of formula I, wherein m is 1, n is 1 or 2, $R^1$ is hydrogen, $C_1$-$C_4$alkyl, $C_3$-$C_5$alkenyl or benzyl, $R^2$ is hydrogen or methyl, $R^3$ is $C_1$-$C_6$alkyl, $C_2$-$C_7$alkenyl, cyclohexyl, phenyl, $C_1$-$C_6$alkoxy, $C_3$-$C_4$alkenyloxy, cyclohexyloxy, phenoxy, or phenoxy substituted by $C_1$-$C_4$alkyl, and $R^4$ is hydrogen, $C_1$-$C_4$alkyl, cyclohexyl, phenyl or a group of the formula II.

3. A compound according to claim 1 of formula I, wherein m is 1, n is 1 or 2, $R^1$ is hydrogen, methyl, allyl or benzyl, $R^2$ is hydrogen or methyl, $R^3$ is $C_1$-$C_4$alkyl, cyclohexyl, phenyl, $C_1$-$C_4$alkoxy, cyclohexyloxy or phenoxy, and $R^4$ is hydrogen, $C_1$-$C_4$alkyl, cyclohexyl, phenyl, or a group of the formula II.

4. A compound according to claim 3, wherein $R^4$ is a group of the formula II.

* * * * *